United States Patent [19]

Dutra

[11] 4,053,505

[45] Oct. 11, 1977

[54] PREPARATION OF N-PHOSPHONOMETHYL GLYCINE

[75] Inventor: Gerard A. Dutra, Ladue, Mo.

[73] Assignee: Monsanto Company, St. Louis, Mo.

[21] Appl. No.: 646,724

[22] Filed: Jan. 5, 1976

[51] Int. Cl.$^2$ ................................................ C07F 9/38
[52] U.S. Cl. .................................. 260/502.5; 260/970
[58] Field of Search .............................. 260/502.5, 970

[56] References Cited

U.S. PATENT DOCUMENTS

| | | | |
|---|---|---|---|
| 3,288,846 | 11/1966 | Irani et al. | 260/502.5 |
| 3,476,799 | 11/1969 | Vogt et al. | 260/502.5 |
| 3,549,728 | 12/1970 | Balde et al. | 260/502.5 |
| 3,799,758 | 3/1974 | Franz | 260/502.5 |
| 3,886,204 | 5/1975 | Geffers et al. | 260/502.4 R |
| 3,923,877 | 12/1975 | Barton | 260/502.5 |

OTHER PUBLICATIONS

Adams et al., "Organic Synthesis" Collective vol. 1, pp. 355–357.

*Primary Examiner*—Joseph E. Evans
*Attorney, Agent, or Firm*—Arnold H. Cole; Donald W. Peterson

[57] ABSTRACT

A herbicidal compound N-phosphonomethyl glycine is prepared by (a) reacting 1,3,5-tricarbohydrocarbonoxymethyl hexahydrotriazine with a di-monovalent hydrocarbon phosphite to form an ester of N-phosphonomethyl glycine which is thereafter (b) hydrolyzed and the N-phosphonomethyl glycine is recovered.

7 Claims, No Drawings

PREPARATION OF N-PHOSPHONOMETHYL GLYCINE

This invention relates to a process for the production of N-phosphonomethyl glycine, which compound is useful as a post-emergent herbicide.

In accordance with the present invention, there is provided a process for producing N-phosphonomethyl glycine, which process comprises (a) reacting a dihydrocarbon phosphite with 1,3,5-tricarboalkoxymethyl-hexahydro-1,3,5-triazine to form a triester of N-phosphonomethyl glycine; (b) hydrolyzing the triester and recovering the N-phosphonomethyl glycine.

The following equation illustrates the reaction:

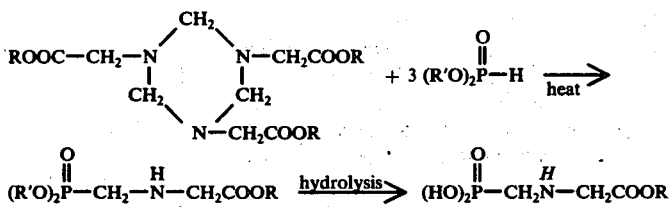

wherein R and R' are monovalent hydrocarbon group or substituted monovalent hydrocarbon groups, the substituents being those which are inert to the reaction. In accordance with the present invention the process is carried out by forming an admixture of the hexahydrotriazine and the phosphite ester and heating the admixture to a temperature sufficiently elevated to initiate the reaction of the phosphite ester with the hexahydrotriazine and thereafter maintaining the admixture at a temperature sufficient to maintain said reaction until said reaction is essentially complete.

In the above reaction the R and R' groups do not enter into the initial reaction between the triazine and the phosphite, therefore the nature of these groups is not critical. These groups are removed when the triester of N-phosphonomethyl glycine is subjected to hydrolysis. Conveniently the R group is an aliphatic radical and the R' group are monocyclic aryl hydrocarbon radicals, substituted aryl radicals, benzyl radicals, substituted benzyl radicals or aliphatic radicals containing from 1 to 6 carbon atoms. Preferably the R groups are lower alkyl radicals containing from 1 to 4 carbon atoms and the R' groups are phenyl, benzyl or lower alkyl radicals.

In step (a) of the process no catalyst is required. The reaction goes essentially to completion by merely heating the reactants to a temperature of from 20° C to 150° C. A catalyst such as a Lewis acid can be employed but no commensurate advantages are obtained thereby.

The temperature at which step (a) of the process is conducted can vary over wide ranges. The temperature employed should be one which is sufficiently elevated so as to initiate and maintain the reaction. Temperatures in the range of from 20° C to 150° C are generally preferred. Temperatures in the range of from 30° C to 120° C are particularly preferred.

The process of this invention can be conducted at atmospheric pressure, sub-atmospheric pressure or super-atmospheric pressure. For convenience and economy, it is preferred to conduct the process of this invention at atmospheric pressure.

Although a solvent is not necessary in conducting the process of this invention, a solvent is sometimes desirable where one or more of the reactants is a solid and also in order to more readily control the temperature of the reaction by conducting the reaction at the boiling point of the solvent employed. The solvents which can be employed in the reaction of the hexahydrotriazine with the phosphite ester are those solvents in which the triazine and the phosphite are soluble and which are themselves inert to reaction with the hexahydrotriazine or phosphite ester. These solvents are for example acetonitrile, benzene, toluene, xylene, mono- and di-chlorobenzene, methylene chloride, chloroform, carbon tetrachloride, ethyl acetate, dimethylformamide, tetrahydrofurane, diethyl ether, ethylene glycol dimethyl ether, diethylene glycol dimethylether, and the like.

In step (a) of the process of this invention a ratio of the triazine to phosphite ester is not critical. As can be seen from the above equation, the molar ratio of phosphite to triazine should be 3 to 1 in order to obtain the best yield. Ratios of from 1 to 10 to 10 to 1 could be employed, however, ratios outside approximately 3 to 1 are unnecessarily wasteful of reagents and may render it more difficult to recover the desired product.

After conducting step (a) of the process of this invention to produce the triester, one can distill off the solvent, if a solvent is employed, before or after the addition of the hydrolysis medium, i.e., the hydrohalic acid or base solution.

The second step (b) of the process of this invention is preferably carried out by refluxing the triester with an aqueous mineral acid such as sulfuric, hydrochloric or hydrobromic acid which is at least 1.0 normal. The hydrochloric acid or hydrobromic acids are preferred since being volatile they are easily removed from the reaction mixture by concentrating the mixture. The concentrated mixture is then cooled to precipitate the N-phosphonomethyl glycine.

The second step (b) of the process of this invention can also be carried out by heating the triester with a caustic solution of an alkali metal or alkaline earth metal hydroxide in a water, or aliphatic alcohol solution or mixtures of such solvents. Inasmuch as a salt would be produced it is necessary to acidify such salts in order to recover the free acid if the free acid is the desired product.

In conducting the hydrolysis step (b) of this invention employing aqueous hydrochloric or hydrobromic acid, it is preferred that the aqueous hydrohalic acid be at least 1.0 normal and even more preferred that it be 2.0 normal. Of course, concentrated aqueous hydrohalic acids can be employed, but no commensurate advantages are obtained thereby.

Where a basic solution is employed to hydrolyze the triester, any of the alkali or alkaline earth metal hydroxides can be employed, the alkali metal hydroxide of lithium, potassium, sodium, rubidium or cesium being preferred, sodium and potassium hydroxides being especially preferred. It is preferred to employ these hydroxides in aqueous solution and at least 0.05 normal. It is of course apparent from the above equation that for best results at least three moles of the alkali metal hydroxide should be employed for each mole of the triester. It is especially preferred to employ about six moles of the alkali metal hydroxide for each mole of the triester of N-phosphonomethyl glycine.

The hydrolysis step (b) of this invention is preferably conducted at temperatures of from 70° to 150° C or even higher. It is especially preferred that the temperature employed be from 85° C to about 125° C for economy and ease of reaction.

The monovalent hydrocarbon radical represented by R and R' are for example lower aliphatic groups such as alkyl, alkenyl and alkynyl groups containing from 1 to 6 carbon atoms and such group substituted with a substituent which is inert to the reaction. Such lower aliphatic groups are methyl, ethyl, propyl, butyl, hexyl, vinyl, allyl, butenyl, butynyl, ethynyl, propynyl, hexynyl and the like, benzyl, phenethyl and the like. R and R' can also be phenyl or naphthyl and such groups substituted with substituents which are inert to the reaction. Illustrative of such inert groups but not limiting are the following groups: lower alkyl, lower alkoxy, lower alkylthio, trifluoromethyl, carbo lower alkoxy, nitro, halo, e.g. chloro, bromo, fluoro or iodo, phenyl, benzyloxy and the like.

The 1,3,5-tricarbohydrocarbonoxymethyl hexahydrotriazines employed in the process of this invention are produced by the reaction of formaldehyde with a hydrocarbon ester of glycine.

The phosphite esters employed in the process of this invention are readily available from commercial sources or can be readily produced by the reaction of a hydrocarbon alcohol with phosphorus trichloride by known methods.

The N-phosphonomethyl glycine produced is useful as a post-emergent contact herbicide particularly against perennial plant species.

The following examples serve to further illustrate this invention. All parts are parts by weight unless otherwise specifically set forth.

EXAMPLE 1

1,3,5-Tricarbethoxymethylhexahydro-1,3,5-triazine (1.38 parts),di-(4-methoxyphenyl)phosphite (3.53 parts containing 0.15 parts of 4-methoxyphenol) and dry benzene (50 ml) were mixed and heated to reflux for 2 hours, and then allowed to stand overnight. Nuclear magnetic resonance spectral analysis indicated that a complete conversion to the ethyl N-[di(4-methoxyphenoxy)-phosphonomethyl]glycinate was obtained. The reaction mixture was concentrated under vacuum, diluted with 2 normal hydrochloric acid (225 ml) and heated to reflux for 2 hours. This reaction mixture was concentrated and then mixed with a mixture of water and methylene chloride. The water layer was then extracted four times with methylene chloride. The aqueous layer was concentrated to yield 1.46 parts of a white solid identified as N-phosphonomethyl glycine and which when mixed with an authentic sample of N-phosphonomethyl glycine showed no differences in a nuclear magnetic resonance spectral analysis.

Workup of the methylene chloride solution with water yielded an additional 0.22 parts of N-phosphonomethyl glycine: total yield 83% of theory.

EXAMPLE 2

1,3,5-Tricarbethoxymethylhexahydro-1,3,5-triazine (1.38 parts) and diphenyl phosphite (2.81 parts) are dissolved in benzene and heated to reflux for 2 hours, and then allowed to stand for 16 hours at ambient temperatures. The reaction mixture is concentrated under vacuum and an excess of dilute sodium hydroxide added and then heated to from 70° C to 100° C for 6 hours. The resultant solution was then neutralized with hydrochloric acid, then allowed to stand at ambient temperature to precipitate the N-phosphonomethyl glycine. By this procedure one obtains substantially theoretical yields of the N-phosphonomethyl glycine.

EXAMPLE 3

Di(4-chlorobenzyl)phosphite (2 parts) was mixed with N-methylene ethyl glycinate trimer (0.69 parts) in dry benzene (~150 parts) and heated to reflux for 20 hours. The benzene was distilled off and the residue diluted with two normal hydrochloric acid (125 parts) and heated to reflux temperature (~100° C) for 22.5 hours. The reaction mixture was concentrated to dryness, dissolved in water and extracted with methylene chloride. The water solution was concentrated to a small volume and allowed to stand to precipitate a white solid. The white solid was identified as N-phosphonomethyl glycine by mixing it with an authentic sample and conducting nuclear magnetic resonance spectral analysis. The total isolated yield was 63% of theoretical.

EXAMPLE 4

1,3,5-Tricarbethoxymethylhexahydro-1,3,5-triazine (5.76 parts) and di(4-methoxyphenyl)phosphite (15.3 parts containing 0.6 parts of 4-methoxyphenol) were mixed and heated to 80° C for from ½ to 1 hour. Nuclear magnetic resonance spectral analysis indicated that a complete conversion to the ethyl N-[di(4-methoxyphenoxy)-phosphonomethyl]glycinate was obtained. The reaction mixture can then be diluted with 2 normal hydrochloric acid (225 ml) and heated to reflux for 2 hours. This reaction mixture is concentrated and then mixed with a mixture of water and methylene chloride. The water layer is then extracted with methylene chloride. The aqueous layer is concentrated to yield N-phosphonomethyl glycine.

EXAMPLE 5

1,3,5-Tricarbomethoxymethylhexahydro-1,3,5-triazine (1.0 part) and diphenyl phosphite (2.93 parts which contained .59 parts of phenol) are mixed and then heated to 80° C for 5 minutes. To the reaction mixture is then added an excess of dilute hydrochloric acid (2.0 N) and then heated to from 70° C to 100° C for 6 hours. The resultant solution is then allowed to stand at ambient temperature to precipitate the N-phosphonomethyl glycine. By this procedure one obtains yields of the N-phosphonomethyl glycine of greater than 80%.

EXAMPLE 6

Diethyl phosphite (1.38 parts) and 1,3,5-tricarbethoxymethylhexahydro-1,3,5-triazine (1.15 parts) were mixed in a pyrex glass reaction vessel and heated to 100° C for 3 hours. Nuclear magnetic resonance spectral analysis indicated that a complete conversion to ethyl N-(diethoxyphoephonomethyl)-glycinate ($n_D$ /25 1.4468). The glycinate is then diluted with concentrated hydrochloric acid and heated to about 100° C for 6 hours and then concentrated to dryness. The N-phosphonomethylglycine is dissolved in a small amount of hot water and then allowed to cool to precipitate essentially pure N-phosphonomethyl glycine.

When hydrobromic acid is employed in the above procedure the same results are obtained.

Although the invention is described with respect to specific modifications, the details thereof are not to be construed as limitations except to the extent indicated in the following claims.

What is claimed is:

1. A process for the production of N-phosphonomethyl glycine which comprises (a) reacting a 1,3,5-tricarbohydrocarbonoxy-methyl-hexahydrotriazine of the formula

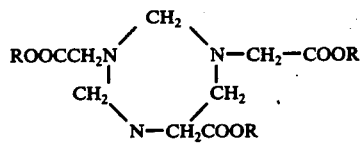

wherein R is a monovalent hydrocarbon or substituted hydrocarbon radical in which the substituent is inert to the reaction; with a phosphite ester of the formula

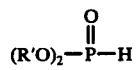

wherein the R' is the same or different radical as defined for R, in the absence of a catalyst, by heating a mixture of said triazine and said ester to a temperature sufficiently elevated to initiate and maintain the reaction to form a triester of N-phosphonomethyl glycine of the formula

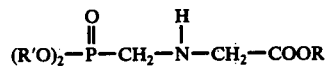

wherein R and R' are as above defined, (b) hydrolyzing the triester and (c) recovering N-phosphonomethyl glycine.

2. A process of claim 1 wherein step (a) is conducted in the presence of a suitable solvent.

3. A process according to claim 2 wherein said triester of N-phosphonomethyl glycine is isolated before the hydrolysis by removing the solvent.

4. A process according to claim 1 wherein R represents an alkyl radical of from 1 to 6 carbon atoms and R' represents a phenyl or substituted phenyl radical.

5. A process in accordance with claim 1 wherein the temperature is between 20° C and 150° C.

6. A process in accordance with claim 1 wherein the hydrolysis is carried out in aqueous hydrohalic acid having a normality of at least 1.0.

7. A process according to claim 2 wherein aqueous hydrohalic acid is added to the reaction mixture before the removal of the solvent.

* * * * *